United States Patent
Mehra et al.

(10) Patent No.: US 10,281,465 B2
(45) Date of Patent: May 7, 2019

(54) SIGNAL AMPLIFICATION IN LATERAL FLOW AND RELATED IMMUNOASSAYS

(71) Applicant: ABAXIS, INC., Union City, CA (US)

(72) Inventors: Rajesh K. Mehra, Hayward, CA (US); Kenneth P. Aron, San Francisco, CA (US); Dennis M. Bleile, San Ramon, CA (US); Jeremy Walker, Castro Valley, CA (US); Cristina Cuesico, Fremont, CA (US)

(73) Assignee: ABAXIS, INC., Union City, CA (US)

(*) Notice: Subject to any disclaimer, the term of this patent is extended or adjusted under 35 U.S.C. 154(b) by 0 days.

(21) Appl. No.: 15/886,290

(22) Filed: Feb. 1, 2018

(65) Prior Publication Data

US 2018/0156790 A1 Jun. 7, 2018

Related U.S. Application Data

(62) Division of application No. 14/688,419, filed on Apr. 16, 2015, now Pat. No. 9,921,218, which is a division
(Continued)

(51) Int. Cl.
*G01N 33/558* (2006.01)
*G01N 33/543* (2006.01)
(Continued)

(52) U.S. Cl.
CPC ............ *G01N 33/54393* (2013.01); *G01N 33/54306* (2013.01); *G01N 33/54313* (2013.01);
(Continued)

(58) Field of Classification Search
CPC .. G01N 33/536; G01N 33/537; G01N 33/541; G01N 33/543; G01N 33/54306;
(Continued)

(56) References Cited

U.S. PATENT DOCUMENTS 4,704,366 A 11/1987 Juarez-Salinas et al.
5,061,381 A 10/1991 Burd
(Continued)

FOREIGN PATENT DOCUMENTS

CN 1417586 A 5/2003
CN 1798976 A 7/2006
(Continued)

OTHER PUBLICATIONS

Bangs Laboratories, Inc., "Lateral Flow Tests," TechNote 303, available at http://www.bangslabs.com/sites/default/files/bangs/docs/pdf/303.pdf, 1999. 6 pages.
(Continued)

*Primary Examiner* — Gailene Gabel
(74) *Attorney, Agent, or Firm* — Cooley LLP

(57) ABSTRACT

The present invention provides methods, devices, compositions (e.g., capture complexes), and kits useful for enhancing the detection of antibodies in a test sample. The methods, devices, and compositions utilize detectable Fc-binding molecules such as Protein A, Protein G, and/or an Fc-specific antibody to amplify the signal of a detected antibody in immunoassays, such as lateral flow assays.

12 Claims, 3 Drawing Sheets

Related U.S. Application Data of application No. 13/682,306, filed on Nov. 20, 2012, now Pat. No. 9,034,656.

(60) Provisional application No. 61/562,302, filed on Nov. 21, 2011.

(51) Int. Cl.
*G01N 33/68* (2006.01)
*G01N 33/569* (2006.01)
*G01N 33/58* (2006.01)

(52) U.S. Cl.
CPC ..... *G01N 33/54386* (2013.01); *G01N 33/558* (2013.01); *G01N 33/56911* (2013.01); *G01N 33/56983* (2013.01); *G01N 33/587* (2013.01); *G01N 33/6854* (2013.01); *G01N 33/6857* (2013.01); *G01N 33/6893* (2013.01); *G01N 2333/20* (2013.01); *G01N 2333/29* (2013.01); *G01N 2469/20* (2013.01); *Y02A 50/57* (2018.01)

(58) Field of Classification Search
CPC ....... G01N 33/54313; G01N 33/54366; G01N 33/54386; G01N 33/54393; G01N 33/558; G01N 33/56911; G01N 33/56983; G01N 33/587; G01N 33/6854; G01N 33/6857; G01N 33/6893; G01N 33/6894; G01N 2333/20; G01N 2333/29; G01N 2469/20; Y02A 50/57

See application file for complete search history.

(56) References Cited

U.S. PATENT DOCUMENTS

| | | |
|---|---|---|
| 5,122,284 A | 6/1992 | Braynin et al. |
| 5,186,844 A | 2/1993 | Burd et al. |
| 5,304,348 A | 4/1994 | Burd et al. |
| 5,457,053 A | 10/1995 | Burd et al. |
| 5,624,597 A | 4/1997 | Buhl et al. |
| 5,693,233 A | 12/1997 | Schembri |
| 5,939,021 A | 8/1999 | Hansen et al. |
| 6,579,726 B1 | 6/2003 | Natan et al. |
| 6,660,381 B2 | 12/2003 | Halas et al. |
| 6,685,986 B2 | 2/2004 | Oldenburg et al. |
| 6,699,724 B1 | 3/2004 | West et al. |
| 6,861,263 B2 | 3/2005 | Natan |
| 6,970,239 B2 | 11/2005 | Chan et al. |
| 7,135,054 B2 | 11/2006 | Jin et al. |
| 7,144,627 B2 | 12/2006 | Halas et al. |
| 7,212,692 B2 | 5/2007 | Yan |
| 7,405,054 B1 | 7/2008 | Hasenbank et al. |
| 7,648,595 B2 | 1/2010 | Jin et al. |
| 7,732,145 B2 | 6/2010 | Kang et al. |
| 7,790,066 B2 | 9/2010 | Wang et al. |
| 8,101,424 B2 | 1/2012 | Geddes |
| 8,110,250 B2 | 2/2012 | Ojima et al. |
| 8,263,418 B2 | 9/2012 | Brennan et al. |
| 8,426,152 B2 | 4/2013 | Gerion et al. |
| 8,597,897 B2 | 12/2013 | Kim et al. |
| 8,628,727 B2 | 1/2014 | Van Duyne et al. |
| 8,697,129 B2 | 4/2014 | Qian et al. |
| 8,753,559 B2 | 6/2014 | Yang et al. |
| 8,784,895 B2 | 7/2014 | Messersmith et al. |
| 8,808,420 B2 | 8/2014 | Adherne et al. |
| 9,034,656 B2 | 5/2015 | Mehra et al. |
| 9,040,310 B2 | 5/2015 | Ashworth-sharpe et al. |
| 9,217,746 B2 | 12/2015 | Geddes |
| 9,308,582 B2 | 4/2016 | Sun et al. |
| 9,835,622 B2 | 12/2017 | Mehra et al. |
| 9,921,218 B2 | 3/2018 | Mehra et al. |
| 2001/0002315 A1 | 5/2001 | Schultz et al. |
| 2006/0240573 A1 | 10/2006 | Kao et al. |
| 2006/0246513 A1 | 11/2006 | Bohannon |
| 2007/0054337 A1 | 3/2007 | Ferning et al. |
| 2007/0092978 A1 | 4/2007 | Mink et al. |
| 2008/0213814 A1 | 9/2008 | Gerion et al. |
| 2009/0018025 A1 | 1/2009 | Shao et al. |
| 2010/0028410 A1 | 2/2010 | Haynie |
| 2010/0062545 A1 | 3/2010 | Geddes |
| 2010/0120057 A1 | 5/2010 | Mehra et al. |
| 2010/0159441 A1 | 6/2010 | Chiang et al. |
| 2010/0184086 A1* | 7/2010 | Callister .......... G01N 33/56911 435/7.1 |
| 2011/0065088 A1* | 3/2011 | Kang ................ G01N 33/526 435/5 |
| 2011/0124125 A1 | 5/2011 | Mehra et al. |
| 2011/0136155 A1 | 6/2011 | Mehra et al. |
| 2011/0275061 A1 | 11/2011 | Weidemaier et al. |
| 2012/0101007 A1 | 4/2012 | Ahern et al. |
| 2012/0208174 A1 | 8/2012 | Galush et al. |
| 2013/0115634 A1 | 5/2013 | Mehra et al. |
| 2013/0130404 A1 | 5/2013 | Mehra et al. |
| 2013/0172207 A1 | 7/2013 | Dai et al. |
| 2013/0189793 A1 | 7/2013 | Qian et al. |
| 2013/0203075 A1* | 8/2013 | Svenson ............. G01N 33/564 435/7.5 |
| 2013/0230717 A1 | 9/2013 | Xia et al. |
| 2014/0105982 A1 | 4/2014 | Oldenburg et al. |
| 2014/0121125 A1 | 5/2014 | Mehra et al. |
| 2014/0170070 A1 | 6/2014 | Qian et al. |
| 2014/0272933 A1 | 9/2014 | Dawson et al. |
| 2015/0004102 A1 | 1/2015 | Hesham et al. |
| 2015/0017258 A1 | 1/2015 | Azzazy et al. |
| 2015/0247846 A1 | 9/2015 | Gerion et al. |
| 2015/0293088 A1 | 10/2015 | Mehra et al. |
| 2016/0047804 A1 | 2/2016 | Mehra et al. |
| 2016/0120978 A1 | 5/2016 | Guler et al. |
| 2016/0202251 A1 | 7/2016 | Goh et al. |
| 2017/0038366 A1 | 2/2017 | Mehra et al. |
| 2018/0059104 A1 | 3/2018 | Mehra et al. |

FOREIGN PATENT DOCUMENTS

| | | | |
|---|---|---|---|
| CN | 102103145 A | 6/2011 | |
| CN | 104105965 B | 7/2016 | |
| JP | H10-132818 A | 5/1998 | |
| JP | 2000-028612 A | 1/2000 | |
| JP | 2000-028614 A | 1/2000 | |
| JP | 2009-516199 A | 4/2009 | |
| WO | WO 2007/047924 A2 | 4/2007 | |
| WO | WO 2007/061793 * | 5/2007 | ....... G01N 33/54393 |
| WO | WO 2007/061793 A2 | 5/2007 | |
| WO | WO 2010/006201 A2 | 1/2010 | |
| WO | WO 2011/063003 A2 | 5/2011 | |
| WO | WO 2011/063235 A2 | 5/2011 | |
| WO | WO 2011/095636 A1 | 8/2011 | |
| WO | WO 2013/067524 A1 | 5/2013 | |
| WO | WO 2013/078227 A1 | 5/2013 | |
| WO | WO 2014/059274 A1 | 4/2014 | |
| WO | WO 2015/160923 A1 | 10/2015 | |
| WO | WO 2016/007942 A1 | 1/2016 | |
| WO | WO 2016/025703 A2 | 2/2016 | |
| WO | WO 2016/134214 A1 | 8/2016 | |
| WO | WO 2017/024163 A1 | 2/2017 | |
| WO | WO 2018/140953 A1 | 8/2018 | |

OTHER PUBLICATIONS

Atanasov, P.A. et al., "Noble metallic nanostructures: preparation, properties, applications", Journal of Physics: Conference Series 514 (2014), pp. 1-8.

Bui, Minh-Phuong N. et al., "Gold nanoparticle aggregation-based highly sensitive DNA detection using atomic force microscopy", Anal Bioanal Chem (2007), 388: 1185-1190.

Dong, P., et al., "Ultrathin Gold-Shell Coated Silver Nanoparticles onto a Glass Platform for Improvement of Plasmonic Sensors." ACS Appl. Mater. Interfaces (2013); 5 (7): 2392-2399.

EP Application No. 12852350.3, Extended European Search Report dated May 13, 2015, 10 pages.

(56) References Cited

OTHER PUBLICATIONS

EP Application No. 15831667.9, Supplementary European Search Report dated Nov. 30, 2017, 9 pages.
Fan, Chao-Ming et al. "A study of double antigen sandwich colloidal gold immunochromatography rapid detection for *Mycobacterium tuberculosis* antibody", US National Library of Medicine Database accession No. NLM21729624 (May 2011), 2 pages.
Gupta, S. et al., "Characterization and optimization of gold nanoparticle-based silver-enhanced immunoassays", Anal. Chem. (2007), 79: 3810-3820.
Gupta, R. et al., "Preparation and characterization of surface plasmon resonance tunable gold and silver films", Journal of Applied Physics (2002), 92(9): 5264-5271.
Helmerhorst, E. et al., "Real-time and label-free bio-sensing of molecular interactions by surface plasmon resonance: A Laboratory Medicine Perspective", Clin Biochem Rev (2012), 33: 161-173.
Hong, W. et al. "Development of an up-converting phosphor technology-based 10-channel lateral flow assay for profiling antibodies against Yersinia pestis", J Microbiol Methods (2010), 83(2): 133-140.
Jia, K., et al., "Strong Improvements of Localized Surface Plasmon Resonance Sensitivity by Using Au/Ag Bimetallic Nanostructures Modified with Polydopamine Films." ACS Appl. Mater. Interfaces (2014); 6 (1): 219-227.
Kvítek, O., et al., "Noble metal nanostructures influence of structure and environment on their optical properties." Journal of Nanomaterials (2013); vol. 2013, Article ID 743684, pp. 1-15, 16 pages.
LamdaGen. Plasmonic ELSA. [online] Apr. 21, 2014 [retrieved Nov. 27, 2015]. Available on the internet at <URL:http://web.archive.org/web/20140421112507/http://lamdagen.eom/lspr-verview/plasmonic-elisa/>, 1 page.
Li, M. et al., "Three-dimensional hierarchical plasmonic nano-architecture enhanced surface-enhanced raman scattering immunosensor for cancer biomarker detection in blood plasma", ACS Nano. (2013), 7(6): 4967-4976.
Mohammed and Desmulliez, "Lab-on-a-chip based immunosensor principles and technologies for the detection of cardiac biomarkers: A Review", Lab Chip (2011), 11(4): 569-595.
Nitin, N. et al., "Oligonucleotide-coated metallic nanoparticles as a flexible platform for molecular imaging agents", Bioconjug Chem. (2007), 18(6): 2090-2096.
Oh, Bo-Ram et al., "Integrated nanoplasmonic sensing for cellular functional immunoanalysis using human blood", ACS Nano. (2014), 8(3): 2667-2676.
Paul, S. et al., "Surface plasmon resonance imaging detection of silver nanoparticle-tagged immunoglobulin", J. R. Soc. Interface (2011), 8: 1204-1211.
PCT/US2012/066108, International Search Report and Written Opinion, dated Mar. 25, 2013, 10 pages.
PCT/US2012/066108, International Preliminary Report on Patentability, dated May 27, 2014, 7 pages.
PCT/US2015/045041, International Search Report and Written Opinion, dated Jul. 26, 2016, 13 pages.
PCT/US2015/045041, International Preliminary Report on Patentability, dated Feb. 14, 2017, 8 pages.
PCT/US2016/045606, International Preliminary Report on Patentability, dated Feb. 6, 2018, 9 pages.
PCT/US2016/045606, International Search Report, dated Oct. 24, 2016, 2 pages.
PCT/US2016/045606, Written Opinion, dated Oct. 24, 2016, 8 pages.
Raphael, M.P. et al., "Quantitative LSPR imaging for biosensing with single nanostructure resolution", Biophysical Journal (2013), 104(1): 30-36.
Ruemmele, J.A. et al., "A localized surface plasmon resonance imaging instrument for multiplexed biosensing", Anal Chem. (2013), 85(9): 4560-4566.
Seekell, K. et al., "Optimization of immunolabeled plasmonic nanoparticles for cell surface receptor analysis", Methods. (2012), 56(2): 310-316.
Shao, Y. et al., "Optical fiber LSPR biosensor prepared by gold nanoparticle assembly on polyelectrolyte multilayer", Sensors (2010), 10: 3585-3596.
Stringer et al., "Development of an optical biosensor using gold nanoparticles and quantum dots for the detection of Porcine Reproductive and Respiratory Syndrome Virus", Sensors and Actuators B: Chemical (2008), 134(2): 427-431.
Tauran, Y. et al., "Molecular recognition by gold, silver and copper nanoparticles", World J Biol Chem. (2013), 4(3): 35-63.
Tokel, O. et al., "Advances in plasmonic technologies for point of care applications", Chem Rev. (2014), 114(11): 5728-5752.
Truong, P.L., et al., "A new method for non-labeling attomolar detection of diseases based on an individual gold nanorod immunosensor." Lab Chip (2011); 11: 2591-2597.
Walters and Parkin, "The incorporation of noble metal nanoparticles into host matrix thin films: synthesis, characterisation and applications", J. Mater. Chem. (2009), 19: 574-590.
Wu et al., "Gold Nanoparticle-Based Enzyme-Linked Antibody-Aptamer Sandwich Assay for Detection of *Salmonella typhimurium*." ACS Applied Materials and Interfaces (2014); 6: 16974-16981.
[Author Unknown], "Sorvall Legend XT Sorvall Legend XTR Instruction Manual," Thermo Fisher Scientific, No. 50119927-4, Feb. 14, 2011 (Feb. 14, 2011), pp. 1-59. Retrieved from the Internet: <http://core.phmtox.msu.edu/Scheduling/ItemDocs/40/XTR_Manual.pdf> on Mar. 7, 2018 (Mar. 7, 2018).
Jana, et al., "Capping Agent-Free Gold Nanostars Show Greatly Increased Versatility and Sensitivity for Biosensing." Anal. Chem. (2015); 87 (7): 3964-3972.
PCT/US2018/015981, International Search Report and Written Opinion, dated Apr. 13, 2018, 22 pages.
Wu, et al., "Bioassay of prostate-specific antigen (PSA) using microcantilevers." Nature Biotechnology (2001); 19: 856-860.
Zhang and Cremer, "Interactions between macromolecules and ions: the Hofmeister series." Blood (2006); 10 (6): 658-663.
Bolduc and Masson, "Advances in surface plasmon resonance sensing with nanoparticles and thin films: nanomaterials, surface chemistry, and hybrid plasmonic techniques." Anal Chem. (2011); 83 (21): 8057-8062. Epub Aug. 29, 2011.
PCT/US2012/066108, Invitation to Pay Additional Fees, dated Jan. 8, 2013, 2 pages.
PCT/US2015/045041, Invitation to Pay Additional Fees, dated Oct. 20, 2015, 3 pages.

* cited by examiner

SIGNAL AMPLIFICATION IN LATERAL FLOW AND RELATED IMMUNOASSAYS

CROSS-REFERENCE TO RELATED APPLICATIONS

This application is a divisional application of U.S. patent application Ser. No. 14/688,419, filed on Apr. 16, 2015, now U.S. Pat. No. 9,921,218, issued on Mar. 20, 2018, which is a divisional of U.S. patent application Ser. No. 13/682,306, filed on Nov. 20, 2012, now U.S. Pat. No. 9,034,656, issued on May 19, 2015, which claims the benefit of U.S. Provisional Application No. 61/562,302, filed on Nov. 21, 2011, which are herein incorporated by reference in their entireties.

BACKGROUND OF THE INVENTION

Immunoassays are frequently used to identify infectious agents, among other uses. Certain immunoassays rely on host immunological responses to a given infectious agent, for instance, by testing for the presence of host antibodies that specifically bind to one or more unique antigens of that infectious agent. Numerous types of immunoassay systems are available for diagnostic purposes, including large, automated central lab systems and relatively simple over-the-counter tests. These immunoassays utilize a broad range of test formats, such as agglutination assays, precipitin assays, enzyme-linked immunoassays, direct fluorescence assays, immuno-histological tests, complement-fixation assays, serological tests, immuno-electrophoretic assays, and lateral flow and flow through tests (i.e., rapid "strip" tests). Immunoassays can provide rapid, simple, and effective diagnoses for a variety of conditions. However, there remains a need in the art for improved immunoassays having increased sensitivity.

SUMMARY OF THE INVENTION

The present invention is based, in part, on the discovery that the addition of detectable Fc-binding molecules (e.g., Protein A-conjugates, Protein G-conjugates, secondary antibody conjugates) can be used for the detection of antibodies in immunoassays, e.g., antigen-based capture or sandwich-type assays. These detectable Fc-binding molecules can be used either alone or in combination with other detectable entities for the detection of antibodies in immunoassays. For example, these Fc-binding molecules can be used to detect antibodies once the antibodies to be detected are captured by antibody-specific binding entities, e.g., antigens. In another example, these Fc-binding molecules can be used as a secondary source for detectable signals, e.g., in combination with another labeled or detectable antibody binding entity such as antigen.

This discovery can be applied to a variety of capture-type assays, related methods, compositions, and kits, as described herein.

Certain embodiments therefore include methods for detecting an antibody in a test sample comprising: (a) contacting the test sample with a first detector to form a first complex comprising the first detector and the antibody, wherein the first detector comprises an Fc-binding molecule conjugated to a first detectable entity; (b) contacting the first complex with a capture entity immobilized on a test region of a surface, wherein the capture entity is capable of specifically binding to the antibody; and (c) detecting the presence of a signal from the first detectable entity in the test region, wherein the presence of the signal is indicative of the presence of the antibody in the test sample. In certain embodiments, the first detector is immobilized to a conjugate region of the surface, wherein the conjugate region does not overlap with the test region of the surface. In specific embodiments, the Fc-binding molecule is protein A, protein G, or both. In certain embodiments, the first detector comprises protein A and protein G each conjugated to the detectable entity. In such embodiments, the ratio of protein A to protein G may be adjusted to optimize the level of signal amplification depending upon the type of immunoglobulin to be detected. For instance, in some embodiments, protein A and protein G are present in a ratio of about 10:1 to about 1:10, more preferably about 5:1 to about 1:5.

In certain embodiments, the capture entity is an antigen or antigenic peptide. In particular embodiments, said antigen or antigenic peptide is from an organism selected from the group consisting of heartworm, e.g., canine heartworm, *Ehrlichia canis, Borrelia burgdorferi, Borrelia afzelii, Borrelia garinii, Anaplasma phagocytophilum*, feline leukemia virus, parvovirus, influenza A strain, influenza B strain, avian influenza virus, respiratory syncytial virus, *Legionella*, adenovirus, rotavirus, feline immunodeficiency virus, human immunodeficiency virus, and Group A *Streptococcus*.

In certain embodiments, the first detectable entity is a metal nanoparticle, metal nanoshell, fluorophore, or colored latex particle. In some embodiments, the metallic nanoparticle or metallic nanoshell is selected from the group consisting of gold particles, silver particles, copper particles, platinum particles, cadmium particles, composite particles, gold hollow spheres, gold-coated silica nanoshells, and silica-coated gold shells.

Certain methods provided herein further comprise contacting the test sample with a second detector, wherein the second detector comprises an antigen or antigenic peptide conjugated to a second detectable entity, said antigen or antigenic peptide being capable of specifically binding to the antibody. In some embodiments, the first and second detector are immobilized on a conjugate region, wherein the conjugate region does not overlap with the test region of the surface. In certain embodiments, the conjugate region further comprises a control detector. The level of signal amplification can be selected by adjusting the ratio of the first detector to the second detector. In certain embodiments, the ratio of the first detector to the second detector is about 20:1 to about 1:20, more preferably about 20:1 to about 1:1.

In specific embodiments, the first and second detectable entities are the same. In more specific embodiments, the first and second detectable entities are both gold nanoparticles. In other embodiments, the first and second detectable entities are different.

In certain embodiments, the surface is a flow path in a lateral flow assay device, a surface of a microtiter plate or a flow path in an analytical rotor.

As noted above, certain embodiments employ a second detector that is conjugated to a detectable entity, where that second detector is an antigen or antigenic peptide. In some of these and related embodiments, the antigen or antigenic peptide is from an organism selected from the group consisting of heartworm, e.g., canine heartworm, *Ehrlichia canis, Ehrlichia chaffeensis, Ehrlichia ewingii, Borrelia burgdorferi, Borrelia afzelii, Borrelia garinii, Anaplasma phagocytophilum, Anaplasma platys*, feline leukemia virus, parvovirus, e.g., canine parvovirus, influenza A strain, influenza B strain, avian influenza virus, respiratory syncytial virus, *Legionella*, adenovirus, rotavirus, feline immunodeficiency virus, human immunodeficiency virus, and Group A *Streptococcus*.

In some embodiments, the surface is a flow path in a lateral flow assay device or a flow path in an analytical rotor. In particular embodiments, the test sample is blood, serum, or plasma.

Also included are antibody detection devices, comprising a sample loading region; a conjugate region, wherein said conjugate region comprises a mobilizable first detector including an Fc-binding molecule conjugated to a first detectable entity; and a test region, wherein said test region comprises an immobilized capture entity capable of specifically binding to the antibody; wherein the sample loading region, the conjugate region and the test region are configured so that in operation a liquid sample when loaded into the sample loading region, is in fluid communication with the conjugate region and the test region. In certain embodiments, the Fc-binding molecule is protein A and/or protein G.

In some embodiments, the capture entity is an antigen or antigenic peptide. In particular embodiments, the antigen or antigenic peptide is from an organism selected from the group consisting of heartworm, e.g., canine heartworm *Ehrlichia canis, Ehrlichia chaffeensis, Ehrlichia ewingii, Borrelia burgdorferi, Borrelia afzelii, Borrelia garinii, Anaplasma phagocytophilum, Anaplasma platys*, feline leukemia virus, parvovirus, e.g., canine parvovirus, influenza A strain, influenza B strain, avian influenza virus, respiratory syncytial virus, *Legionella*, adenovirus, rotavirus, feline immunodeficiency virus, human immunodeficiency virus, and Group A *Streptococcus*.

In particular embodiments, the first detectable entity is a metal nanoparticle, metal nanoshell, fluorophore, or colored latex particle. In specific embodiments, the metallic nanoparticle or metallic nanoshell is selected from the group consisting of gold particles, silver particles, copper particles, platinum particles, cadmium particles, composite particles, gold hollow spheres, gold-coated silica nanoshells, and silica-coated gold shells.

In some embodiments, the device further comprises a control region in fluid communication with a liquid sample when it is loaded to the sample loading region. In certain embodiments, the control region comprises an immobilized binding partner capable of specifically binding a control detector.

In particular embodiments, the first detector comprises protein A or protein G conjugated to a first detectable entity and said immobilized binding partner is an anti-protein A or anti-protein G antibody.

Some devices further comprise an absorbent pad positioned downstream of the test region. In certain devices, the conjugate region is positioned upstream of the sample loading region. In some embodiments, the conjugate region is positioned downstream of the sample loading region. In some embodiments, the sample loading region comprises a blood separator material. In certain instances the conjugate region further comprises a mobilizable second detector, wherein the second detector comprises an antigen or antigenic peptide conjugated to a second detectable entity, said antigen or antigenic peptide being capable of specifically binding to the antibody. The ratio of the first detector (e.g. Fc-binding molecule, such as protein A and/or protein G, conjugated to a first detectable entity) to the second detector (antigen/antigenic peptide conjugated to a second detectable entity) can be adjusted to select a desired level of signal amplification. In some embodiments, the ratio of the first detector to the second detector is about 20:1 to about 1:20. In other embodiments, the ratio of the first detector to the second detector is about 20:1 to about 1:1.

In particular embodiments, the first and second detectable entities are the same. In specific embodiments, the first and second detectable entities are gold nanoparticles. In other embodiments, the first and second detectable entities are different.

In particular embodiments, for example, for detection of anti-microbial antibodies, the antigen or antigenic peptide is from an organism selected from the group consisting of heartworm, e.g., canine heartworm *Ehrlichia canis, Ehrlichia chaffeensis, Ehrlichia ewingii, Borrelia burgdorferi, Borrelia afzelii, Borrelia garinii, Anaplasma phagocytophilum, Anaplasma platys*, feline leukemia virus, parvovirus, e.g., canine parvovirus, influenza A strain, influenza B strain, avian influenza virus, respiratory syncytial virus, *Legionella*, adenovirus, rotavirus, feline immunodeficiency virus, human immunodeficiency virus, and Group A *Streptococcus*.

Also included are kits comprising one or more of the detection devices and systems described herein, and instructions for using the device or system to detect an antibody in a test sample. Certain kits further comprise a second detector and instructions for combining the second detector with the test sample prior to application to the sample loading region of the detection system, wherein said second detector comprises an antigen or antigenic peptide conjugated to a second detectable entity, said antigen or antigenic peptide being capable of specifically binding to the antibody. In some embodiments, the instructions provide combining the second detector with the test sample such that the second detector will be present in a particular ratio with the first detector to achieve a desired level of signal amplification.

Also included are methods of detecting an antibody in a test sample comprising applying the test sample to the sample loading region of one or more of the detection devices or systems described herein, and detecting the presence or absence of a signal from the first detectable entity in the test region. Some methods further comprise combining a second detector with the test sample prior to application to the sample loading region of the detection system, wherein said second detector comprises an antigen or antigenic peptide conjugated to a second detectable entity, said antigen or antigenic peptide being capable of specifically binding to the antibody.

Certain embodiments relate to one or more capture complexes that comprise a capture entity, an antibody in a test sample, and a first detector, wherein the capture entity binds to the antibody and wherein the first detector comprises a Fc-binding molecule conjugated to a first detectable entity and binds to the Fc region of the antibody. Certain of these and related embodiments further comprise a second detector, wherein the second detector specifically binds to the variable region of the antibody. In some embodiments, the capture complex is immobilized on a test region of a surface.

DETAILED DESCRIPTION

Figure 1:
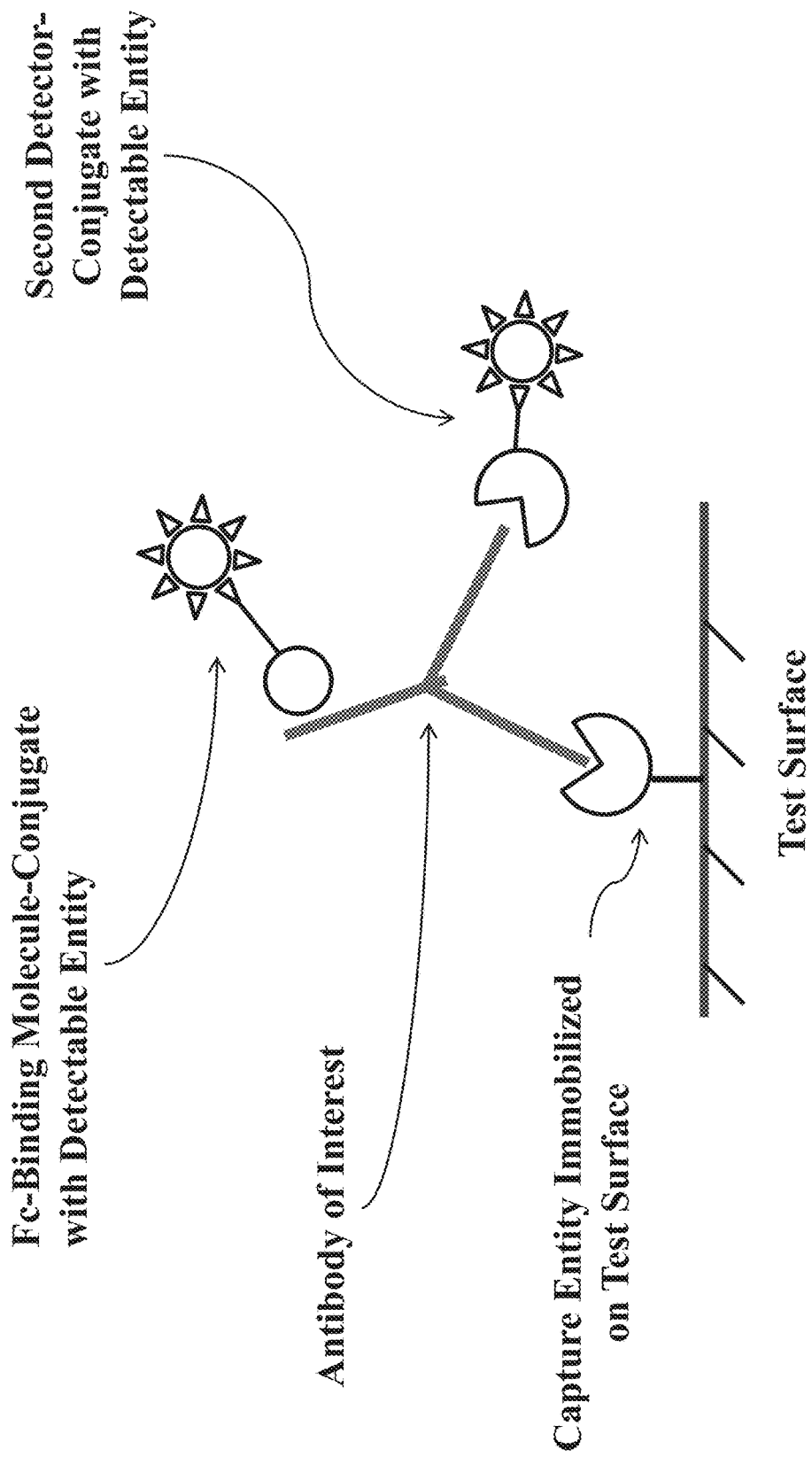
FIG. 1 illustrates one example of a capture complex of the invention, with an antibody of interest being captured by a capture entity (e.g., antibody-specific antigen conjugated to BSA) immobilized to a test surface (e.g., nitrocellulose), a detectable Fc-binding molecule-conjugate (e.g., Protein A- or Protein G-colloidal gold conjugate) bound to the Fc region of a target antibody, and optionally a second detectable conjugate (e.g., antigen-colloidal gold conjugate) bound to the variable region of the antibody of interest.

As used herein, the following terms shall have the following meanings:

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "peptide" and "polypeptide" and "protein" are used interchangeably herein to refer to a polymer of amino acid residues and to variants and synthetic and naturally occurring analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers and naturally occurring chemical derivatives thereof.

An "increased" or "enhanced" amount is optionally a "statistically significant" amount, and may include an increase that is about 1.1, 1.2, 1.3, 1.4, 1.5, 1.6, 1.7, 1.8, 1.9, 2.0, 2, 3, 4, 5, 6, 7, 8, 9, 10, 15, 20, 30 or more times (including all integers, ranges and decimal points in between and above 1, e.g., 2.5, 3.6, 3.7. 3.8, etc.) the amount or value (e.g., signal or value such as a Reactivity score) relative, for example, to an antibody test performed without a detectable Fc-binding molecule. A "increased" or "enhanced" value or amount may also include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 200%, 300%, 400%, 500% or more increase in the amount or value relative, for example, to an antibody test performed without a detectable Fc-binding molecule.

All publications, patents and patent applications cited herein are hereby incorporated by reference in their entirety.

Methods

In one aspect, the present invention includes methods for detecting an antibody in a test sample. In certain embodiments, these methods relate, in pertinent part, to contacting the test sample with an Fc-binding molecule conjugated to a first detectable entity (i.e., a detectable Fc-binding molecule-conjugate) to form a first complex, contacting the first complex with a capture entity immobilized on a test region of a surface, wherein the capture entity is capable of specifically binding to the antibody, and detecting the presence of a signal from the detectable Fc-binding molecule-conjugate in the test region. Here, the presence of the signal is indicative of the presence of the antibody in the test sample.

The reactants of these methods can be contacted in any order or sequence. For instance, the test sample can be mixed with the detectable Fc-binding molecule-conjugate prior to application to the surface, or these two reactants can be applied separately to the surface, sequentially or at the same time, in the same or different place on the surface. When added separately, the reactants will come into contact with one another as they spread or flow through the test surface, for example, by capillary or other action. In particular embodiments, the detectable Fc-binding molecule-conjugate is immobilized beforehand to a conjugate region of the surface, which does not overlap with the test region of the surface. In certain of these embodiments, the test sample can be applied to the surface, where it flows via capillary or other action through the conjugate region and the test region, and thereby contacts the Fc-binding molecule and the capture entity. If an antibody of interest is present in the sample, then it will form a detectable complex with the detectable Fc-binding molecule and the capture entity. In specific embodiments, the Fc-binding molecule is protein A, protein G, protein A/G, protein L or any combination thereof, e.g., as a mixture or a fusion protein thereof.

Certain methods provided herein further comprise contacting the test sample with a second detector molecule. In these embodiments, the second detector can be any suitable antibody binding entity, e.g., an antigen or antigenic peptide conjugated to a second detectable entity and capable of specifically binding to the antibody. The combination, e.g., the conjugate of second detector and second detectable entity is sometimes referred to as a "detectable antibody-specific antigen-conjugate" or a "detectable antigen-conjugate," which includes peptide antigens and non-peptide antigens. In some embodiments, the first and second detectable entities are the same, i.e., the Fc-binding molecule-conjugate and the detectable-antigen-conjugate are conjugated to the same type of detectable entity, such as a gold particle. In other embodiments, the first and second detectable entities are different. In specific embodiments, the first and second detectable entities are both gold nanoparticles, to create colloidal gold conjugates (CGC). In these and related embodiments, the detectable Fc-binding molecule can be referred to as an "Fc-binding molecule-CGC"; specific examples include Protein A-CGCs, Protein G-CGCs, protein A/G-CGCs, and protein L-CGCs. In some embodiments, the Fc-binding molecule is a secondary antibody or a fragment thereof capable of binding to the Fc region of the antibody in the test sample while the second detector can be any suitable antibody binding entity, e.g., antigen or antigenic peptide, etc.

Similar to above, the reactants in these methods can be contacted in any order or sequence. As one example, the test sample can be mixed with the detectable Fc-binding molecule-conjugate, the detectable antigen-conjugate, or both, prior to application to the surface, or these three reactants can be applied separately to the surface, sequentially or at the same time, in the same or different place on the surface. When added separately, the reactants will come into contact with one another as they spread or flow through the test surface, for example, by capillary or other action.

In some embodiments, the Fc-binding molecule-conjugate is immobilized to a conjugate region of the surface, which does not overlap with the test region, and the test sample and the detectable antigen-conjugate are applied separately or together to the surface. In other embodiments, the detectable antigen-conjugate is immobilized to a conjugate region of the surface, which does not overlap with the test region, and the test sample and the detectable Fc-binding molecule-conjugate are applied separately or together to the surface. In certain embodiments, the detectable Fc-binding molecule-conjugate and the detectable antigen-conjugate are both immobilized to a conjugate region of the surface, which does not overlap with the test region of the surface, and the test sample is applied to the test surface. After application to the surface, the test sample (alone or in combination with the other reactants), can flow or spread throughout the surface via capillary or other action, through the conjugate region (if present) and the test region, and thereby contact the detectable Fc-binding molecule-conjugate, the detectable antigen-conjugate, and the capture entity. If an antibody of interest is present in the sample, it will form one or more detectable complexes with these reactants, and thereby indicate the presence of the antibody in the sample. Persons skilled in the art will realize that these exemplary combinations are non-limiting, and that other possibilities are possible.

In certain embodiments, the conjugate region further comprises a control detector, for instance, an antibody that specifically binds to the Fc-binding molecule. Other types of control regions will be apparent to persons skilled in the art.

A test sample is usually a biological sample obtained from a subject that has or is suspected of having an antibody of interest, such as an antibody that is specific for an infectious agent. A biological sample is preferably easy to obtain and may include blood, serum or plasma derived from a venous blood sample or even from a finger prick. Tissue from other body parts or other bodily fluids, such as cerebro-spinal fluid (CSF), saliva, gastric secretions, mucus, urine, feces, etc., are known to contain antibodies and may be used as a source of a test sample. In other embodiments, the sample is a tissue (e.g., a tissue homogenate), extract from a bodily organ, or a cell lysate. In certain embodiments, the subject is a wild animal (e.g., a deer or rodent, such as a mouse, chipmunk, squirrel, etc.). In other embodiments, the subject is a lab animal (e.g., a mouse, rat, guinea pig, rabbit, monkey, primate, etc.). In other embodiments, the subject is a domesticated or feral animal (e.g., a dog, a cat, a horse). In still other embodiments, the subject is a human.

An antibody, also referred to as an immunoglobulin, is a Y-shaped protein of the immune system that specifically identifies foreign objects or antigens, such as the components of bacteria, yeasts, parasites, and viruses. Each tip of the 'Y' of an antibody contains an antigen-binding site that is specific for a particular epitope on an antigen, allowing these two structures to bind together with precision. The production of a given antibody is increased upon exposure to an antigen (e.g., a microbial antigen) that specifically interacts with that antibody. Hence, the detection of antigen-specific antibodies in a sample from a subject can inform whether that subject is currently exposed to, or has been previously exposed to, a given microbe, such as a virus, bacteria, fungus, or parasite.

The fragment crystallizable region (Fc region) is the tail region of an antibody that interacts with cell surface Fc receptors and certain proteins of the complement system. In IgG, IgA and IgD antibody isotypes, the Fc region is composed of two identical protein fragments, derived from the second and third constant domains of the antibody's two heavy chains. IgM and IgE Fc regions contain three heavy chain constant domains ($C_H$ domains 2-4) in each polypeptide chain. The Fc regions of IgG antibodies bears a highly conserved N-glycosylation site. The N-glycans attached to this site are predominantly core-fucosylated diantennary structures of the complex type. In addition, small amounts of these N-glycans also bear bisecting GlcNAc and α-2,6 linked sialic acid residues. The Fab region of an antibody contains variable sections that define the target-specificity of the antibody, and in contrast, the Fc region of all antibodies in a class are the same for each species; they are constant rather than variable.

An "antigen-binding site," or "binding portion" of an antibody, refers to the part of the immunoglobulin molecule that participates in antigen binding. The antigen binding site is formed by amino acid residues of the N-terminal variable ("V") regions of the heavy ("H") and light ("L") chains.

Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

An antibody typically comprises all or a portion of an Fc region, to facilitate detection by an Fc-binding molecule, and may also comprise one or more antigen-binding sites, to facilitate detection by an antibody-specific binding agent, such as an antigen or antigenic peptide. The antibodies can be, e.g., of IgG, IgE, IgD, IgM, or IgA type. Generally, IgM and/or IgA antibodies are detected, e.g., for detection at early stages of infection.

An Fc-binding molecule includes any binding agent that specifically binds to the Fc region of an antibody or any region that is outside of the variable region of an antibody. In certain embodiments, an Fc-binding molecule is not an antibody or antigen-binding fragment thereof. In other embodiments, the Fc-binding molecule is an Fc-specific secondary antibody, e.g., a rabbit anti-dog antibody, a goat anti-dog antibody. In certain embodiments, an Fc-binding molecule is a secondary antibody against the antibody to be detected in a test sample. General examples of Fc-binding molecules include polypeptides, soluble receptors, adnectins, small peptides, peptide mimetics, small molecules, aptamers, etc., that specifically bind to the Fc-region of an immunoglobulin. Specific examples of Fc-binding molecules include Protein A, Protein G, Protein A/G fusion proteins, Protein L, and fragments and variants thereof which retain the ability to specifically bind to the Fc region of an antibody.

Protein A is a 40-60 kDa MSCRAMM (microbial surface components recognizing adhesive matrix molecules) surface protein found in the cell wall of *Staphylococcus aureus*, and is encoded by the spa gene. Wild-type Protein A is composed of five homologous Ig-binding domains that fold into a three-helix bundle, and which can individually bind to the Fc regions of an antibody. Protein A binds with high affinity to human IgG1 and IgG2 and with moderate affinity to human IgM, IgA and IgE.

Protein G is an immunoglobulin-binding protein expressed in group C and G Streptococcal bacteria (see, e.g., Sjobring et al., *J Biol Chem.* 266: 399-405, 1991). The NMR solution structure (see Lian et al., *Journal of Mol. Biol.* 228:1219-1234, 1992) and the crystal structure (see Derrick and Wigley, *Journal of Mol. Biol.* 243:906-918, 1994) of Protein G have been resolved to 1 Angstrom. Protein A and Protein G are well-known in the art and commercially available in a variety of conjugated and un-conjugated forms.

Also included are functional variants and fragments of full-length or wild-type versions of Protein A and Protein G. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to the wild-type sequence of Protein A and/or Protein G. A functional fragment of can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 450, 500 or more contiguous or non-contiguous residues of wild-type Protein A and/or Protein G. Variants and fragments of Protein A and Protein G typically retain specific binding for the Fc region of one or more immunoglobulin isotypes.

Percent sequence identity has an art recognized meaning and there are a number of methods to measure identity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used, with an affine gap search with a gap open penalty of −12 and a gap extension penalty of −2.

Fusion proteins that comprise Fc-binding polypeptides are also contemplated, including Protein A fusions and Protein G fusions. Fc-binding molecules can be fused to all or a portion of another Fc-binding molecule, or to one or more heterologous polypeptides. A specific example of a Protein A/G fusion protein combines four Fc-binding domains from Protein A with two from Protein G (see, e.g., Sikkema, J. W. D., *Amer. Biotech. Lab,* 7:42, 1989; and Eliasson et al., *J. Biol. Chem.* 263, 4323-4327, 1988); however, other combinations can be used. Fusion partners (e.g., a peptide or other moiety) can be used to improve purification, improve solubility, enhance expression of the polypeptide in a host cell, aid in detection, and stabilize the polypeptide, etc. Examples of fusion partners include carrier proteins (e.g., serum albumin such as bovine serum albumin), beta-galactosidase, glutathione-S-transferase, histidine tag(s), etc.

A capture entity can be any binding agent that specifically binds to an antibody of interest, that is, a target antibody, such as a microbe-specific antibody, to be detected by the methods and devices described herein. Typically, the capture entity specifically binds to the variable region of an antibody, and thus contains one or more epitopes that are specific for the antigen-binding site(s) of an antibody. In certain embodiments, a capture entity is not an antibody or an antigen-binding fragment thereof. In particular embodiments, a capture entity is an antigen or an antigenic peptide that specifically binds to an antibody of interest. Exemplary antigens and antigenic peptides are described below. Also included are soluble receptors, adnectins, peptide mimetics, small molecules, aptamers, etc., that specifically bind to an antibody of interest, that is, an antibody that is to be detected according to the methods provided herein.

As noted above, a capture entity is usually attached to or immobilized on a test surface or substrate, such as a solid or semi-solid support. The attachment can be covalent or non-covalent, and can be facilitated by a moiety associated with the capture entity that enables covalent or non-covalent binding, such as a moiety that has a high affinity to a component attached to the carrier, support or surface. For example, a capture entity can be associated with a ligand, such as biotin, and the component associated with the surface can be a corresponding ligand receptor, such as avidin. Alternatively, a capture entity can be associated with a ligand receptor, such as avidin, and the component associated with the surface can be a corresponding ligand, such as biotin. The capture entity can be attached to or immobilized on the test surface or substrate either prior to or after the addition of a sample containing antibody during an immunoassay.

In particular embodiments, the test surface is a bead, dot blot, a flow path in a lateral flow assay device, or a flow path in an analytical rotor. For example, the capture entity can be attached or immobilized on a porous membrane, such as a PVDF membrane (e.g., an Immobilon™ membrane), a nitrocellulose membrane, polyethylene membrane, nylon membrane, or a similar type of membrane. In other embodiments, the test surface or substrate is a tube or a well, such as a well in a plate (e.g., a microtiter plate) suitable for use in an ELISA or other sandwich-type assay. In some embodiments, the test surface or substrate is a sensor, such as an electrochemical, optical, or opto-electronic sensor.

Such test surfaces or substrates can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. A test surface or substrate can be sintered, fine particles of polyethylene, commonly known as porous polyethylene, for example, 0.2-15 micron porous polyethylene from Chromex Corporation (Albuquerque, N. Mex.), Porex™, etc. All of these test surface or substrate materials can be used in suitable shapes, such as films, sheets, or plates, or they may be coated onto or bonded or laminated to appropriate inert carriers, such as paper, glass, plastic films, or fabrics.

Suitable methods for immobilizing capture entities such as peptides on solid phases include ionic, hydrophobic, covalent interactions and the like. Specific or semi-specific binding to a solid or semi-solid carrier, support or surface, can be achieved by the capture entity having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin, neutravidin, or an analogue thereof. An alternative is a situation in which the moiety has an amino acid sequence of six consecutive histidine residues (e.g. 6x-His tag) and the carrier comprises a Nitrilotriacetic Acid (NTA) derivative charged with $Ni^{++}$ or $Co^{++}$ ions. Further to above, suitable carriers, supports, and surfaces include, but are not limited to, beads (e.g., magnetic beads, colloidal particles or nanoparticles, such as colloidal gold, or nanoparticles comprising silica, latex, polystyrene, polycarbonate, or PDVF), latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles.

As noted above, antigens and antigenic peptides can be used as capture entities and/or as antibody-specific detectors. A selected antigen or antigenic peptide is capable of specifically binding to a target antibody, most often via one or both of the antibody's antigen binding sites. Hence, the term "antigen," as used herein, refers to a molecule capable of being specifically bound by an antibody via at least one antigen-binding site of the antibody. An antigen can comprise one or more epitopes, the particular contiguous or non-contiguous region(s) of the antigen that specifically bind to the antigen-binding site of the antibody. An epitope can be a linear epitope, sequential epitope, or a conformational epitope.

An antigen can be, for example, a peptide or a modified form thereof, or a non-peptide antigen such as a small molecule. As noted above, antigens can also include soluble receptors, adnectins, peptide mimetics, small molecules, aptamers, etc., that specifically bind to an antibody of interest.

When used as capture entities, or "capture antigens," antigens or antigenic peptides are usually unlabeled and are immobilized or otherwise attached to a test surface. For certain embodiments, capture antigens can be fused or conjugated to or complexed with one or more heterologous proteins, such as bovine serum albumin or multiple antigen peptides (MAPS), to facilitate attachment to the test surface or other purpose.

For use as antibody-specific detectors, the antigens or antigenic peptides are usually conjugated to a detectable entity and thereby form a "detectable antigen-conjugate." In certain embodiments, these detectable antigen-conjugates are also fused or conjugated to or complexed with one or more heterologous proteins such as bovine serum albumin or MAPS. Detectable antigen-conjugates can be designed for either direct or indirect detection, as described below.

Fusion proteins that comprise antigenic peptides are also contemplated. Antigenic peptides can be fused to all or a portion of one or more antigenic peptides having the same or different binding specificity (e.g., having one or more of the same or different epitopes), or to one or more heterologous polypeptides. Fusion partners (e.g., a peptide or other moiety) can be used to improve purification, improve solubility, enhance expression of the peptide in a host cell, aid in detection, stabilize the antigenic peptide, facilitate immobilization onto a test surface, etc. Examples of fusion partners include carrier proteins (e.g., serum albumin such as bovine serum albumin), beta-galactosidase, glutathione-S-transferase, histidine tag(s), etc.

Antigens and antigenic peptides and other antibody-specific binding agents can be derived from a variety of sources. Particular embodiments include those that are derived from microbial sources, including viruses, bacteria, fungi, and parasites. Specific examples include antigens that are from any one or more of heartworm, e.g., canine heartworm, *Ehrlichia canis, Borrelia burgdorferi, Borrelia afzelii, Borrelia garinii, Anaplasma phagocytophilum*, feline leukemia virus, parvovirus, e.g., canine parvovirus, influenza A strain, influenza B strain, avian influenza virus, respiratory syncytial virus, human immunodeficiency virus (HIV), *Legionella*, adenovirus, Group A *Streptococcus*, feline immunodeficiency virus (Hy), rotavirus, etc. Examples of *Borrelia* antigens for the detection of Lyme disease antibodies can be found in U.S. application Ser. No. 13/667,909, U.S. Patent Publication No. US 2011/0136155, and WO 2011/063003

(each of which is incorporated by reference in its entirety). Examples of *Ehrlichia* antigens for the detection of *Ehrlichia* antibodies can be found in U.S. Application No. 61/712,578, U.S. Patent Publication No. 2011/0124125, and WO2011/063235 (each of which is incorporated by reference in its entirety).

Antigenic peptides for use according to the methods described herein can be prepared by synthetic chemistry (i.e., a "synthetic peptide"). In other embodiments, antigenic peptides can be produced biologically (i.e., by cellular machinery, such as a ribosome). In certain embodiments, antigenic peptides are isolated. As used herein, an "isolated" peptide is a peptide that has been produced either synthetically or biologically and then purified, at least partially, from the chemicals and/or cellular machinery used to produce the peptide. In certain embodiments, an isolated peptide is substantially purified. The term "substantially purified," as used herein, refers to a molecule, such as a peptide, that is substantially free of cellular material (proteins, lipids, carbohydrates, nucleic acids, etc.), culture medium, chemical precursors, chemicals used in synthesis of the peptide, or combinations thereof. A peptide that is substantially purified has less than about 40%, 30%, 25%, 20%, 15%, 10%, 5%, 2%, 1% or less of the cellular material, culture medium, other polypeptides, chemical precursors, and/or chemicals used in synthesis of the peptide. Accordingly, a substantially pure molecule, such as a peptide, can be at least about 60%, 70%, 75%, 80%, 85%, 90%, 95%, 98%, or 99%, by dry weight, the molecule of interest. An isolated peptide can be in water, a buffer, or in a dry form awaiting reconstitution, e.g., as part of a kit. An isolated peptide can be in the form of a pharmaceutically acceptable salt. Suitable acids and bases that are capable of forming salts with the peptides of the present invention are well known to those of skill in the art, and include inorganic and organic acids and bases.

An antibody of interest, or antigen-binding fragment thereof, is said to "specifically bind," "immunologically bind," and/or is "immunologically reactive" to a capture entity or antibody-specific detector (e.g., antigen or antigenic peptide) if it reacts at a detectable level (within, for example, a lateral flow assay, western blot, or ELISA assay) with the entity or detector, and does not react detectably in a statistically significant manner with unrelated polypeptides or agents under similar conditions. The term "specifically bind" can also mean that a capture entity or antibody-specific detector has a higher affinity (e.g., a higher degree of selectivity) for an antibody of interest than for other antibodies in a sample.

Immunological binding, as used in this context, generally refers to the non-covalent interactions of the type which occur between an immunoglobulin molecule and an antigen for which the immunoglobulin is specific. The strength, or affinity of binding such as immunological binding interactions can be expressed in terms of the dissociation constant ($K_d$) of the interaction, wherein a smaller $K_d$ represents a greater affinity. Immunological binding properties of selected polypeptides can be quantified using methods well known in the art (see, e.g., Davies et al., *Annual Rev. Biochem.* 59:439-473, 1990). In certain illustrative embodiments, an antibody has an affinity for a capture entity or an antibody-specific detector (e.g., antigen or antigenic peptide) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. As another example, a capture entity or antibody-specific detector can have an affinity for the antibody of at least about 1.5-fold, 2-fold, 2.5-fold, 3-fold, or higher than for other antibodies in the sample.

Similarly, an Fc-binding molecule is said to "specifically bind" to an Fc region of an immunoglobulin if it reacts at a detectable level with the Fc region, and does not react detectably in a statistically significant manner with unrelated polypeptides or agents under similar conditions. In some illustrative embodiments, an Fc-binding molecule has an affinity for the Fc-region of a selected immunoglobulin isotype of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. Certain Fc-binding molecules have a stronger or weaker affinity for one or more immunoglobulin isotypes relative to others.

Such affinity or degree of specificity can be determined by a variety of routine procedures, including, e.g., competitive binding studies. In an ELISA assay, a positive response is defined as a value 2 or 3 standard deviations greater than the mean value of a control or group of controls.

As noted above, certain detector molecules such as Fc-binding molecules, antigens, and/or antigenic peptides are conjugated to a detectable entity. Conjugation is typically achieved by covalent attachment. Detectable entities include "directly detectable entities," such as metal nanoparticles, metal nanoshells, colored latex particles, radioisotopes, and fluorophores, and "indirectly detectable entities," which often rely on ligand-receptor interactions to achieve signaling. In the former case, the detector molecule (e.g., antigenic peptide, Fc-binding molecule such as Protein A/G) is conjugated to the directly detectable entity. In the latter case, the detector molecule is conjugated to a ligand, which then interacts with its ligand-receptor, the latter being conjugated to a directly detectable entity—or vice versa. Examples of ligands include biotin (e.g., via a cysteine or lysine residue), lipid molecules (e.g., via a cysteine residue), and carrier proteins (e.g., serum albumin). Attachment to ligands, such as biotin, can be useful for associating the detector with ligand receptors, such as avidin, streptavidin, or neutravidin. Avidin, streptavidin, neutravidin, in turn, can be linked to a directly detectable entity (e.g., a signaling moiety that can be visualized, such as colloidal gold, a fluorescent moiety, or an enzyme such as horseradish peroxidase or alkaline phosphatase). Alternatively, the detector molecules can be fused or linked to a ligand receptor, such as avidin, streptavidin, or neutravidin, thereby facilitating an association with the corresponding ligand, which, in turn, is linked to a directly detectable entity. Examples of other ligand-receptor pairs are well-known in the art and can similarly be used.

Examples of directly detectable entities (or signaling moieties) include radioisotopes, fluorophores, dyes, enzymes, nanoparticles, colored latex particles, chemiluminescent markers, light-emitting dyes, and others described herein and known in the art.

Examples of radioisotopes that can be used as directly detectable entities include $^{32}P$, $^{33}P$, $^{35}S$, $^{3}H$, and $^{125}I$. These radioisotopes have different half-lives, types of decay, and levels of energy which can be tailored to match the needs of a particular protocol. For example, $^{3}H$ is a low energy emitter which results in low background levels, however this low energy also results in long time periods for autoradiography and other measurements.

Examples of fluorophores or fluorochromes that can be used as directly detectable entities include fluorescein, tetramethylrhodamine, Texas Red, and a number of others (e.g., Haugland, *Handbook of Fluorescent Probes—9th Ed.*, 2002, Molec. Probes, Inc., Eugene Oreg.; Haugland, *The*

Handbook: A Guide to Fluorescent Probes and Labeling Technologies—10th Ed., 2005, Invitrogen, Carlsbad, Calif.). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-($\varepsilon$-carboxypentyl)-3'-ethyl-5,5'-dimethyloxacarbocyanine (CYA); 6-carboxy fluorescein (FAM); 5 & 6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750.

Very small particles, termed nanoparticles, also can be used as directly detectable entities. These particles usually range from 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

Quantum dots can also be used as directly detectable entities. Quantum dots are fluorescing crystals 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

Detecting the presence of a signal can be achieved by any means appropriate to the label or detectable entity being employed by the assay. For example, the detection step may include visibly inspecting the capture complex for a color change, or inspecting the capture complex for a physical-chemical change. Physical-chemical changes may occur with oxidation reactions or other chemical reactions. They may be detected by eye, using a spectrophotometer, or the like.

A signal is typically indicative of the presence of an antibody of interest when it is stronger than the signal of negative control; however, not all tests require a negative control. In some instances, but not necessarily, the strength of a positive signal can be numerically quantified and is indicative of the presence of the antibody when that strength is statistically significant relative to a control. In some instances, the routine knowledge and experience with a particular test type establishes when a signal is positive or negative, and thus indicates the presence or absence of an antibody of interest.

As one example, the signal from certain lateral flow assay devices can be measured according to the Reactivity score, a score of 0-5 (including decimal points in between) where a stronger and more positive signal is given a higher number score. A negative control will typically have a score that is closer to zero, for example, about 0.25 or less.

The detection signal can be optimized, for example, by adjusting the ratio of the individual reactants. One example includes adjusting the ratio of (i) the detectable Fc-binding molecule conjugate(s) and (ii) detectable antigen/antigenic peptide conjugate(s) as follows: a ratio (e.g., molar ratio) of (i):(ii) of about 1:200, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or 200:1, including all ratios and ranges of ratios in between. In some embodiments, the ratio of the detectable Fc-binding molecule conjugate to a detectable antigen/antigenic peptide conjugate is from about 20:1 to about 1:20, preferably from about 20:1 to about 1:1, and more preferably from about 16:1 to about 2:1. In certain embodiments, the Fc-binding molecule in the detectable conjugate is Protein A, Protein G, Protein A/G fusion proteins, Protein L, or fragments and variants thereof which retain the ability to specifically bind to the Fc region of an antibody.

In some embodiments, a mixture of protein A and protein G is used as the Fc-binding molecule-conjugates, wherein each protein A and protein G molecule is conjugated to a detectable entity. In such embodiments where protein A and protein G are both used as the detectable Fc-binding molecule conjugate, the detection signal may be optimized by altering the ratio of protein A to protein G depending on the type of immunoglobulin class to be detected. As explained supra, protein A and protein G have different binding affinities to the Fc regions of different immunoglobulin classes (e.g., of IgG, IgE, IgD, IgM, or IgA). Accordingly, the ratio of protein A to protein G may be adjusted based upon the immunoglobulin class one desires to detect. By way of example, if one desires to detect predominantly IgM immunoglobulins, a lower ratio of protein A to protein G (i.e. a higher amount of protein G conjugate relative to protein A conjugate) may be used. On the other hand, if one desires to detect predominantly IgG immunoglobulins, a higher ratio of protein A to protein G (i.e. a higher amount of protein A conjugate relative to protein G conjugate) may be used. Exemplary ratios (e.g., molar ratios) of protein A to protein G conjugates include, but are not limited to, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, and 20:1. In some embodiments, the ratio of protein A conjugate to protein G conjugate is from about 10:1 to about 1:10, preferably from about 5:1 to about 1:5, and more preferably about 2:1 to about 1:2. In one embodiment, the ratio of protein A conjugate to protein G conjugate is about 1:1.

In certain embodiments, the detection signal may be further optimized by adjusting protein A to protein G ratios in relation to the amount of detectable antigen/antigenic peptide conjugate(s). For instance, in some embodiments, the ratio (e.g., molar ratio) of protein A conjugate to protein G conjugate to detectable antigen/antigenic peptide conjugate may be from about 20:20:1 to about 1:1:20, from about 10:10:1 to about 2:2:1, or from about 4:2:1 to about 1:2:1.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (Coligan et al., editors, John Wiley & Sons, Inc). In some embodiments, the detecting step comprises performing a lateral flow immunoassay. In certain embodiments, the detecting step comprises performing an ELISA assay. In other embodiments, the detecting step comprises spinning the sample in an analytical rotor. In still other embodiments, the detecting step comprises analyzing the sample with an electrochemical, optical, or optoelectronic sensor.

A particularly useful assay format is a lateral flow immunoassay format. As one non-limiting example, reporter or detector molecules including an Fc-binding molecule (e.g., Protein A and/or G) and optionally an antibody specific-antigen are labeled with a detectable entity (e.g., colloidal gold) and then dried and placed on a glass fiber pad (the sample application pad or conjugate pad). Unlabeled antigen or antigenic peptide (i.e., the capture entity) is immobilized on a membrane, such as nitrocellulose or a PVDF (polyvinylidene fluoride) membrane (e.g., an Immobilon™ membrane). When a solution of sample (blood, serum, etc.) is applied to the sample application pad (or flows through the conjugate pad), it dissolves the labeled detector(s), which then bind to the antibodies in the sample, if present. The resulting complexes are then transported into the next membrane (PVDF or nitrocellulose containing the capture entity) by capillary action. If antibodies against the capture entity are present, then they complex with the detector(s) and the diagnostic capture entity on the membrane, thereby generating a signal (e.g., a band that can be seen or visualized).

As another non-limiting example, the sample pad is not striped with the detector molecules (i.e., detectable Fc-binding molecules, detectable antigen-conjugates), that is, the sample pad contains no conjugate region of pre-immobilized detector molecules. All other components are essentially the same as described above, where unlabeled antigen or antigenic peptide (i.e., the capture entity) is immobilized on a membrane, such as nitrocellulose or a PVDF (polyvinylidene fluoride) membrane (e.g., an Immobilon™ membrane). The test sample (blood, serum, etc.) is pre-mixed with one or both detector molecules, and then applied to the sample pad. Alternatively, the test sample and the detector molecules are applied to the sample pad separately, at the same time or sequentially. Other combinations will be apparent to persons skilled in the art. Regardless of the order in which they are mixed or applied, the resulting complexes of the antibodies in the sample and the detector molecules(s) are then transported into the next membrane (PVDF or nitrocellulose containing the capture entity) by capillary action. If antibodies against the capture entity are present, then they complex with the detectors and the diagnostic capture entity on the membrane, thereby generating a signal (e.g., a band that can be seen or visualized).

In specific embodiments, the methods include contacting the test sample with a Protein A and/or Protein G-colloidal gold conjugate (CGC) to form a first complex, contacting the first complex with a peptide antigen immobilized on a test region of a nitrocellulose or PVDF membrane, where the peptide antigen is derived from a microbial source and specifically binds to an antibody of interest (e.g., an anti-bacterial, anti-viral, anti-parasitic, anti-fungal antibody). The peptide antigen can be conjugated to BSA or synthesized as MAPS. The presence of a signal from the Protein A-CGC and/or Protein G-CGC in the test region is indicative of the presence of the antibody in the test sample.

Certain methods further include contacting the test sample with a peptide antigen-CGC conjugate, which comprises the same peptide antigen described above. In certain embodiments, the Protein A/G-CGC or secondary antibody-CGC or a combination thereof and the peptide antigen-CGC are immobilized on a conjugate region of the membrane (or a separate but connected membrane) in a way that does not overlap with the test region. In other embodiments, the Protein A/G-CGC or secondary antibody-CGC or a combination thereof and the peptide antigen-CGC are not immobilized on the membrane, but are rather applied to the surface along with the test sample, at the same time or sequentially. The combined signal from the Protein A/G-CGC and/or the secondary antibody-CGC and the peptide antigen-CGC indicates the presence of the antibody in the test sample, and is typically stronger than the signal from a test performed with the peptide antigen-CGC alone, i.e. without the Protein A-CGC, Protein G-CGC, or the secondary antibody-CGC. In specific embodiments, the peptide antigen is a *Borrelia* antigen (naturally existing or synthesized, e.g., identical to or mimic the naturally existing antigen), and test sample is from a subject suspected of having Lyme disease. A positive signal identifies the presence of Lyme disease-specific antibodies in the sample. In other embodiments, the peptide antigen is an *Ehrlichia* antigen (naturally existing or synthesized, e.g., identical to or mimic the naturally existing antigen), and the subject is suspected of having Ehrlichiosis, a tick-borne bacterial infection caused by bacteria of the family Anaplasmataceae, genera *Ehrlichia* and *Anaplasma*.

Another assay for the screening of blood products or other physiological or biological fluids is an enzyme linked immunosorbent assay, i.e., an ELISA. Typically in an ELISA, capture entities (e.g., antibody-specific antigens) are adsorbed to the surface of a microtiter well directly or through a capture matrix (e.g., an antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing an antibody of interest. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with one or more detector molecules, including an Fc-binding molecule (e.g., Protein A and/or Protein G) and optionally another antibody-specific antigen (usually the same as the capture entity) that are conjugated to an enzyme or other label by standard procedures and is dissolved in blocking buffer. The label can be chosen from a variety of enzymes, including horseradish peroxidase (HRP), beta-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where Lyme disease is not endemic, or by other such conventional definitions. In the case of a very specific assay, OD+2 SD can be used as a cutoff value. Conditions for performing ELISA assays are well-known in the art.

It should be understood by one of skill in the art that any number of conventional protein assay formats, particularly immunoassay formats, may be designed to utilize the various embodiments described herein. This invention is thus not limited by the selection of the particular assay format, and is believed to encompass assay formats that are known to those of skill in the art.

Phrases such as "sample containing an antibody" or "detecting an antibody in a sample" are not meant to exclude samples or determinations (e.g., detection attempts) where no antibody is contained or detected. In a general sense, this invention involves assays to determine whether an antibody produced in response to infection by an infectious microbe is present in a sample, irrespective of whether or not it is detected.

Conditions for reacting antigens/peptides and antibodies so that they react specifically are well-known to those of skill in the art. See, e.g., Current Protocols in Immunology (Coligan et al., editors, John Wiley & Sons, Inc).

Devices and Compositions

In another aspect, the present invention includes devices for detecting an antibody in a sample. Certain embodiments include antibody detection devices or antibody detection systems, comprising a sample loading region, a conjugate region, and a test region. The conjugate region typically does not overlap with the test region; however, the sample region and these two regions are configured so that in operation a liquid sample when loaded into the sample loading region, is in fluid communication with the conjugate region and the test region. Usually, the test sample flows through or communicates with the conjugate and test regions via capillary action. The conjugate region comprises a mobilizable Fc-binding molecule conjugated to a first detectable entity (i.e., a detectable Fc-binding molecule-conjugate, such as a Protein A and/or Protein G-conjugate, or an Fc-specific secondary antibody-conjugate), and the test region comprises an immobilized capture entity capable of specifically binding to the antibody. Each of these features is described elsewhere herein.

In some embodiments, the device further comprises a control region in fluid communication with a liquid sample when it is loaded to the sample loading region. Again, the liquid sample may flow through or communicate with the control region via capillary action. In certain embodiments, the control region comprises an immobilized binding partner capable of specifically binding a control detector. As one example, the control region comprises an anti-protein A antibody, an anti-protein G antibody, or any of the mammalian IgGs reactive with protein A or protein G.

Some devices further comprise an absorbent pad positioned downstream of the test region. In certain devices, the conjugate region is positioned upstream of the sample loading region. In some embodiments, the conjugate region is positioned downstream of the sample loading region. In some embodiments, the sample loading region comprises a blood separator material.

In certain instances, the conjugate region further comprises a mobilizable second detector, wherein the second detector comprises an antigen or antigenic peptide conjugated to a second detectable entity, said antigen or antigenic peptide being capable of specifically binding to the antibody. In certain embodiments, the first (e.g., detectable Fc-binding molecule) and second (e.g., detectable antigen-conjugate) detectors have the same type of detectable entity. In other embodiments, the first and second detectors have different types of detectable entities. In particular embodiments, the ratio (e.g. molar ratio) of the first detector to the second detector is adjusted to achieve a desired level of signal amplification. For instance, the ratio of the first detector (e.g., detectable Fc-binding molecule, such as protein A/protein G) to the second detector (e.g., detectable antigen-conjugate) can be about 1:200, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or 200:1, including all ratios and ranges of ratios in between. In some embodiments, the ratio of the detectable Fc-binding molecule conjugate to a detectable antigen/antigenic peptide conjugate is from about 20:1 to about 1:20, preferably from about 20:1 to about 1:1, and more preferably from about 16:1 to about 2:1. In embodiments in which both protein A and protein G conjugates are used as the detectable Fc-binding molecules, the ratio of protein A conjugate to protein G conjugate can be adjusted to optimize the detection signal based upon the immunoglobulin class to be detected as described above. Suitable ratios (e.g. molar ratios) of protein A conjugate to protein G conjugate include, but are not limited to, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, and 20:1. In some embodiments, the ratio of protein A conjugate to protein G conjugate is from about 10:1 to about 1:10, preferably from about 5:1 to about 1:5, and more preferably about 2:1 to about 1:2. In one embodiment, the ratio of protein A conjugate to protein G conjugate is about 1:1.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices (e.g., lateral flow immunoassay devices), dipsticks, and immunocapillary or immunochromatographic immunoassay devices.

In some embodiments, the device is a lateral flow immunoassay. In certain embodiments, the device is a microtiter plate suitable for an ELISA assay. In other embodiments, the device is suitable for use in an analytical rotor. In still other embodiments, the device comprises an electrochemical, optical, or opto-electronic sensor.

Figure 2:
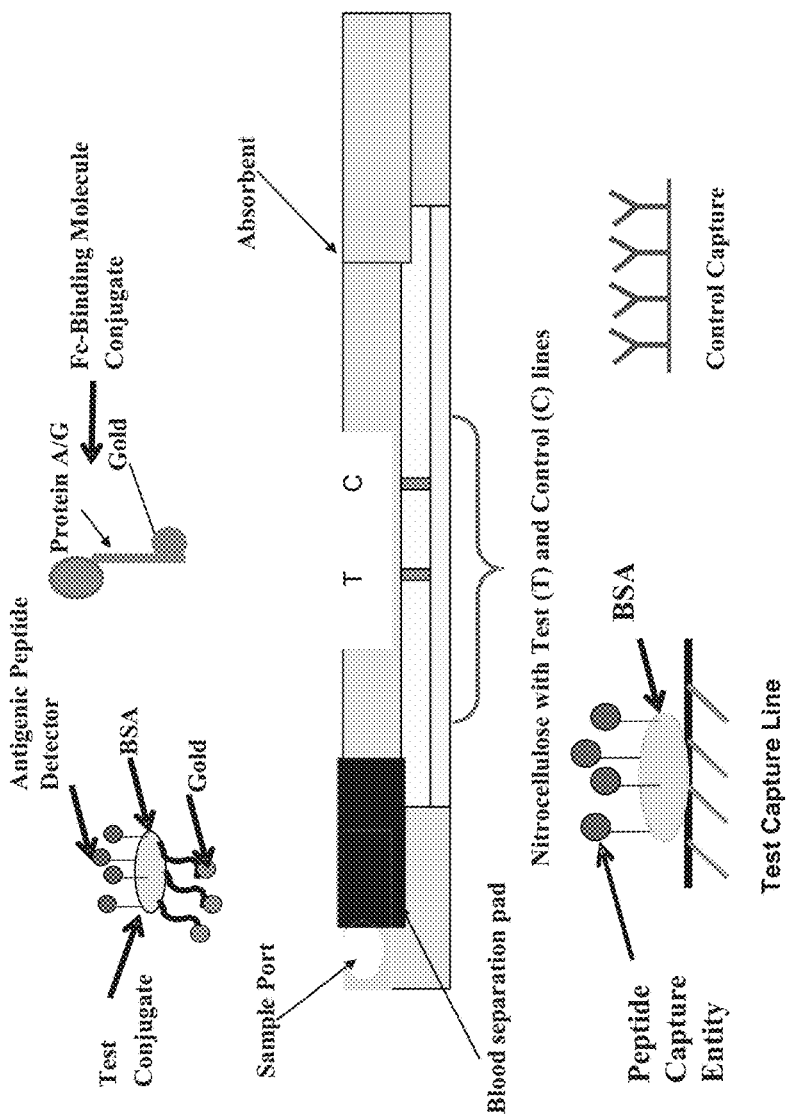
FIG. 2 illustrates one example of a lateral flow device and method according to the present invention. Antigenic peptides specific to an antibody of interest are linked to the carrier protein bovine serum albumin (BSA) and the resulting BSA-peptide conjugates are used as capture on nitrocellulose. This same antigenic peptide is further conjugated to colloidal gold, which serves as the label in this exemplary assay. The signal produced is then further amplified by addition of Protein A/G-gold conjugate(s) to the conjugate mixture.

In certain embodiments, a lateral flow device is constructed using a sample/blood separation pad, nitrocellulose membrane, and an upper wick placed in a housing (see, e.g., FIG. 2). The nitrocellulose membrane is striped with a test line or region comprising a capture entity, such as an unlabeled, antibody-specific antigen (e.g., a peptide antigen or non-peptide antigen), and optionally a control line or region containing an antibody that is reactive to an Fc-binding molecule (indicated below). A sample suspected of containing an antibody of interest can be pre-mixed with a detectable Fc-binding molecule-conjugate, and then applied to the lateral flow assay device. Or, rather than pre-mixing, the sample and the Fc-binding molecule can be applied at the same time or sequentially to the assay device, in any order.

Alternatively, the nitrocellulose membrane is prepared as above and further striped with a conjugate line or region comprising a detectable Fc-binding molecule-conjugate, where the conjugate and test regions do not overlap. In some embodiments, a sample suspected of containing an antibody of interest can then be applied to the lateral flow assay device. In other embodiments, a sample suspected of containing an antibody of interest can be pre-mixed with a detectable antigen-conjugate, which specifically binds to the antibody (typically having the same binding specificity as the capture entity), and then applied to the lateral flow assay device. Similar to above, rather than pre-mixing, the sample and the detectable antigen-conjugate can be applied at the same time or sequentially to the assay device, in any order In some embodiments, a lateral flow device is constructed using a sample/blood separation pad, nitrocellulose membrane, and an upper wick placed in a housing (see, e.g., FIG. 2). The nitrocellulose membrane is striped with a test line or region comprising a capture entity, such as an unlabeled, antibody-specific antigen (e.g., a peptide antigen or non-peptide antigen), optionally a control line or region containing an antibody that is reactive to an Fc-binding molecule (indicated below), and a conjugate line or region comprising a detectable antigen-conjugate, which specifically binds to the antibody (typically having the same binding specificity as the capture entity). The conjugate and test regions usually do not overlap. A sample suspected of containing an antibody of interest can be pre-mixed with a detectable Fc-binding molecule-conjugate, and then applied to the lateral flow assay device. Also, rather than pre-mixing, the sample and the Fc-binding molecule can be applied at the same time or sequentially to the assay device, in any order. In one exemplary embodiment, two-port devices may also be used for sequential application of a test sample, conjugate and chase buffer.

In certain lateral flow devices, the nitrocellulose membrane is striped with a test line or region comprising a capture entity, such as an unlabeled, antibody-specific antigen (e.g., a peptide antigen or non-peptide antigen), optionally a control line or region containing an antibody that is reactive to an Fc-binding molecule (indicated below), and a conjugate line or region comprising a detectable Fc-binding molecule and a detectable antigen-conjugate, which specifically binds to the antibody (typically having the same binding specificity as the capture entity). A sample suspected of containing an antibody of interest can then be applied to the lateral flow assay device.

In an exemplary device for the detection of Lyme-specific antibodies, a lateral flow device is constructed using a sample/blood separation pad, nitrocellulose membrane, and an upper wick placed in a housing (see, e.g., FIG. 2). The nitrocellulose membrane is striped with a test line or region comprising a mixture of peptides that mimic or simulate *Borrelia* antigens (see, e.g., U.S. application Ser. No. 12/948,209) and a control line or region comprising any Protein A- or Protein G-reactive immunoglobulin (e.g., anti-Protein A IgG, mouse, human or other Protein A-reactive IgG, etc.). A sample suspected of containing antibodies to *Borrelia burgdorferi* can be mixed with either colloidal gold conjugates of Protein A and/or G (Protein A/G-CGC), or (ii) a mixture of Protein A/G-CGC and colloidal gold conjugates of the *Borrelia* antigens (*Borrelia* antigen-CGC). This sample conjugate mixture can then be applied to the lateral flow assay device.

Alternatively, a lateral flow device is constructed as above, but where the nitrocellulose pad is striped with one or more conjugate regions, separate from the test region. The conjugate regions can include, for example, (i) Protein A/G-CGC alone, (ii) *Borrelia* antigen-CGC alone, or (iii) a combination of Protein A/G-CGC and *Borrelia* antigen-CGC. As used herein or anywhere else in this application, *Borrelia* antigen, *Ehrlichia* antigen, or any antigen or antigenic peptide includes a mixture of synthetic peptides mimicking or simulating natural *Borrelia* antigen, natural *Ehrlichia* antigen or any natural antigen, respectively. In certain embodiments, for instance in (i) or (iii), the test sample is applied by itself to the lateral flow device without any pre-mixing. In other embodiments, for instance in (i), the sample can be pre-mixed with *Borrelia* antigen-CGC and then applied to the lateral flow device. In some embodiments, for instance in (ii), the sample can be pre-mixed with Protein A/G-CGC and then applied to the lateral flow device. However, these exemplary combinations are non-limiting, and other possibilities will be apparent to persons skilled in the art.

Capture complexes comprising the Protein A/G-CGC, the antibody in the sample, and the optional *Borrelia* antigen-CGC are formed during transport through the sample/blood separation pad and migration through the optional conjugate line(s) and the test line(s). Depending on the circumstances (e.g., optional use of *Borrelia* antigen-CGC), a complex or sandwich is formed of immobilized and unlabeled *Borrelia* antigen, the antibody, and labeled Protein A/G-CGC. In the presence of *Borrelia* antigen-CGC, a complex or sandwich is formed of unlabeled *Borrelia* antigen, the antibody, labeled *Borrelia* antigen-CGC, and labeled Protein A/G-CGC. The addition of Protein A/G-CGC to the latter complex further amplifies the signal from the labeled *Borrelia* antigen-CGC. In certain embodiments, increased amplification can be achieved by adjusted the ratios of all the reactants, as described herein and known in the art.

In an exemplary device for the detection of Ehrlichiosis-specific antibodies, a lateral flow device is constructed using a sample/blood separation pad, nitrocellulose membrane, and an upper wick placed in a housing. The nitrocellulose membrane is striped with a test line or region comprising an *Ehrlichia* antigen and a control line or region comprising any Protein A- or Protein G-reactive immunoglobulin (e.g., anti-Protein A IgG). A sample suspected of containing antibodies to *Ehrlichia* (e.g., *E. canis, E. chaffeensis, E. ewingii,*) can be mixed with either colloidal gold conjugates of Protein A and/or G (Protein A/G-CGC), or (ii) a mixture of Protein A/G-CGC and colloidal gold conjugates of the *Ehrlichia* antigen (*Ehrlichia* antigen-CGC). This sample conjugate mixture can then be applied to the lateral flow assay device.

Alternatively, a lateral flow device is constructed as above, but where the nitrocellulose pad is striped with one or more conjugate regions, separate from the test region. The conjugate regions can include, for example, (i) Protein A/G-CGC alone, (ii) *Ehrlichia* antigen-CGC alone, or (iii) a combination of Protein A/G-CGC and *Ehrlichia* antigen-CGC. In certain embodiments, for instance in (i) or (iii), the test sample is applied by itself to the lateral flow device without any pre-mixing. In other embodiments, for instance in (i), the sample can be pre-mixed with *Ehrlichia* antigen-CGC and then applied to the lateral flow device. In some embodiments, for instance in (ii), the sample can be pre-mixed with Protein A/G-CGC and then applied to the lateral flow device. However, these exemplary combinations are non-limiting, and other possibilities will be apparent to persons skilled in the art.

Capture complexes comprising the Protein A/G-CGC, the antibody in the sample, and the optional *Ehrlichia* antigen-CGC are formed during transport through the sample/blood separation pad and migration through the optional conjugate line(s) and the test line(s). Depending on the circumstances (e.g., optional use of *Ehrlichia* antigen-CGC), a complex or sandwich is formed of immobilized and unlabeled *Ehrlichia* antigen, the antibody, and labeled Protein A/G-CGC. In the presence of *Ehrlichia* antigen-CGC, a complex or sandwich is formed of unlabeled *Ehrlichia* antigen, the antibody, labeled *Ehrlichia* antigen-CGC, and labeled Protein A/G-CGC. The addition of Protein A/G-CGC to the latter complex further amplifies the signal from the labeled *Ehrlichia* antigen-CGC. In certain embodiments, increased amplification can be achieved by adjusted the ratios of all the reactants, as described herein and known in the art.

In one embodiment of a microtiter plate suitable for an ELISA, a capture entity is immobilized on a surface, such as a ninety-six-well ELISA plate or equivalent solid phase that is coated with streptavidin or an equivalent biotin-binding compound, such as avidin or neutravidin, at an optimal concentration in an alkaline coating buffer and incubated at 4° C. overnight. After a suitable number of washes with standard washing buffers, an optimal concentration of biotinylated forms of an Fc-binding molecule and optionally the same antigen used as the capture entity is dissolved in a conventional blocking buffer, is applied to each well. A sample is then added, and the assay proceeds as described herein and known in the art.

In another aspect, the present invention provides compositions related to the detection of an antibody in a sample. Certain embodiments relate to one or more capture complexes that comprise a capture entity, an antibody in a test sample, and a first detector, wherein the capture entity binds to the antibody and wherein the first detector comprises a Fc-binding molecule conjugated to a first detectable entity and binds to the Fc region of the antibody. Certain embodiments further comprise a second detector, wherein the second detector specifically binds to the variable region of the antibody. In some embodiments, the capture complex is immobilized on a test region of a surface, such as a solid or semi-solid support. For example, in certain embodiments, the solid support is a bead (e.g., a colloidal particle or a nanoparticle), a flow path in a lateral flow immunoassay device, a flow path in an analytical rotor, or a tube or a well (e.g., in a plate). See FIG. 1 for an illustration of these and related embodiments, including the optional second-detector conjugate and the optional test surface.

In particular embodiments, the complex comprises an antibody of interest (e.g., an anti-microbial antibody, such as an anti-viral, anti-bacterial, anti-fungal, or anti-parasitic antibody), a Protein A- and/or Protein G-conjugate, an immobilized, antibody-specific antigen, and optionally an antigen-conjugate. In certain embodiments, the Protein A- and/or Protein-G conjugate comprises a gold nanoparticle (e.g., a Protein A-CGC or Protein G-CGC—"colloidal gold conjugate"), and the antigen-conjugate comprises a gold nanoparticle (e.g., an antigen-CGC). In some embodiments, the antigen-conjugate or antigen-CGC comprises a microbial antigen, such as a viral, bacterial, fungus, or parasitic antigen, as described herein and known in the art. In specific embodiments, the antigen-conjugate or antigen-CGC includes a Lyme disease-specific antigen, such as a *Borrelia* antigen (see supra). In other embodiments, the antigen-conjugate or antigen-CGC includes an Ehrlichiosis disease-specific antigen, such as an *Ehrlichia* antigen.

Kits

In yet another aspect, the invention provides kits. In certain embodiments, the kits comprise a device or system of the invention, as described herein. In certain embodiments, the kits comprise two, three, four, or more devices or systems of the invention.

Reagents for particular types of assays can also be provided in kits of the invention. Thus, the kits can include a population of nanoparticles, beads (e.g., suitable for an agglutination assay or a lateral flow assay), or a plate (e.g., a plate suitable for an ELISA assay). In other embodiments, the kits comprise a device, such as a lateral flow immunoassay device, an analytical rotor, or an electrochemical, optical, or opto-electronic sensor. The population of nanoparticles, beads, the plate, and the devices are useful for performing an immunoassay. For example, they can be useful for detecting formation of an antibody-peptide complex comprising an antibody from a sample, an antigenic peptide (labeled and/or unlabeled), and an Fc-binding molecule.

In certain embodiments, an antigen (or a mixture of different antigens) is conjugated to a detectable entity such as a gold nanoparticle, that same antigen (or mixture of antigens) is also attached to or immobilized on a plate, a nitrocellulose test surface, or other test surface or device, and an Fc-binding molecule is conjugated to a detectable entity such as a gold nanoparticle. In specific kits, an antigenic peptide is conjugated to a gold nanoparticle and is optionally conjugated to BSA, that same antigen (without the gold particle but optionally conjugated to BSA) is immobilized onto a defined test region or strip of a nitrocellulose surface, and Protein A and/or Protein G is conjugated to a gold nanoparticle, optionally as part of a kit containing a lateral flow assay device. In some embodiments, the Protein A- and/or Protein G-gold particle conjugate is immobilized onto a separate region of the nitrocellulose surface, i.e., a conjugate region, which does not overlap with the test region.

In addition, the kits can include various diluents and buffers, labeled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for an Fc-binding molecule such as Protein A and/or Protein G, or a cocktail of two or more of the antibodies, purified or semi-purified extracts of antigens or antibodies as standards, monoclonal antibody detector antibodies, an anti-mouse, anti-dog, anti-chicken, or anti-human antibody with indicator molecule conjugated thereto, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex.

Such kits provide a convenient, efficient way for a clinical laboratory to diagnose infection by a microbial agent, especially pathogenic microbial agents, as described elsewhere herein and known in the art. Such kits can also provide a convenient, efficient way for a clinical laboratory to diagnose other conditions related to the presence of any antibody of interest. For example, certain auto-immune disorders can associate with certain types of antibodies. Thus, to the extent that disease-related antibody/antigen combinations are known, the present invention can provide sensitive and accurate diagnostics of such diseases. Specific kits provide detection of *Borrelia*, such as a *B. burgdorferi*, and thus aid in the diagnosis of Lyme disease.

In certain embodiments, the kits further comprise an instruction. For example, in certain embodiments, the kits comprise an instruction indicating how to use the kit detect an antibody, such as an antibody to a microbial antigen (e.g., *Borrelia* antigen, *Ehrlichia* antigen), or to diagnose a disease, such as a microbial-related disease (e.g., Lyme disease, Ehrlichiosis). In certain embodiments, the kits comprise an instruction indicating how to use a population of beads, a plate, or a device (e.g., lateral flow device) to detect an antibody to a microbial antigen such as a *Borrelia* antigen or *Ehrlichia*, or to diagnose a microbial-related disease such as Lyme disease (Borreliosis) or Ehrlichiosis. In certain embodiments, the kits provide instructions for combining the detectable Fc-binding molecule, the antibody-specific, detectable antigen-conjugate or antigenic peptide-conjugate, and the test sample in any order prior to application to the sample loading region of the detection system (e.g., a lateral flow assay device, microtiter plate, analytical rotor). In some embodiments, the kits include instructions for combining the detectable antigen-conjugate or antigenic peptide-conjugate with the test sample such that the detectable antigen-conjugate or antigenic peptide-conjugate will be present in a particular ratio with the detectable Fc-binding molecule to achieve a desired level of signal amplification. The kits may also provide instructions for optimization of buffers, optimization of the ratios of the various components (e.g., Fc-binding molecule, antigen or antigenic peptide, test sample), and optimization of the order of the mixture and application steps (e.g., mix all components prior to application, mix only certain components and apply others separately).

The peptides, compositions and devices comprising the peptides, kits and methods of the invention offer a number of advantages. For example, they allow for simple, inexpensive, rapid, sensitive and accurate detection of antibodies of interest, and diagnostic of related conditions, without significant false positive or background signals. This allows for an accurate and sensitive diagnosis, even of samples containing very low, and even otherwise undetectable, levels of antibodies.

EXAMPLES

Figure 3:
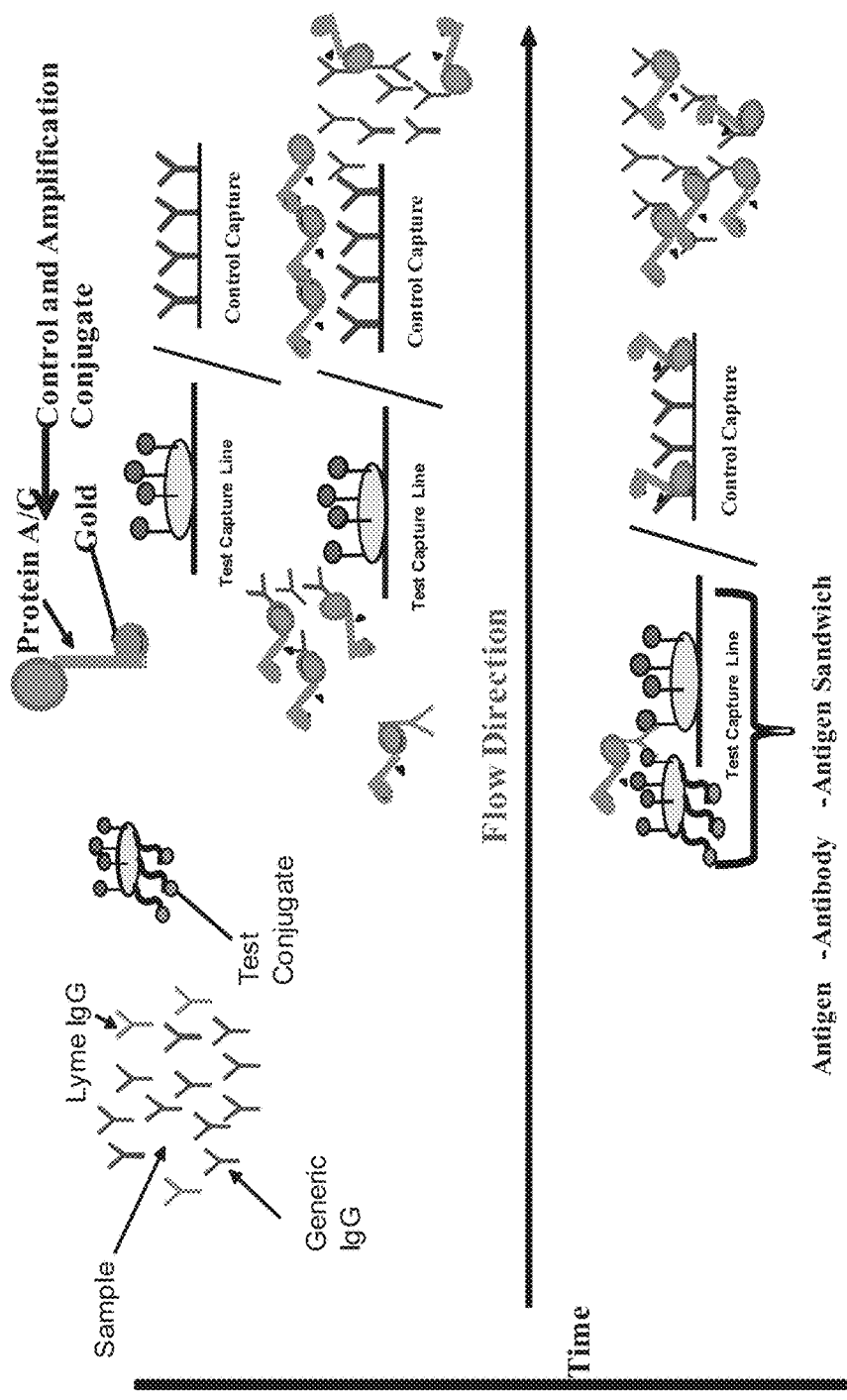
FIG. 3 illustrates the sample flow over time of a Lyme-disease specific lateral flow assay, using the lateral flow device shown in FIG. 2. In this exemplary assay, one drop of blood, serum, or plasma (approximately 15-20 µL via transfer pipette) is mixed with four drops of colloidal gold conjugate solution (approximately 30 µL from a dropper bottle) in a reaction tube. One drop from the resulting reaction mixture is transferred to the sample port of the test cassette that is placed on a flat surface. The blood separation pad filters blood cells from whole blood (see FIG. 2). Plasma (or serum) and the *B. burgdorferi* antibody-conjugate complexes migrate to the nitrocellulose membrane containing the test and the control regions. The application of three (3) drops (approximately 60 µL from a dropper bottle) of chase buffer (one minute after sample application) moves the whole mixture through nitrocellulose towards the upper absorbent pad that keeps on pulling the liquid. The antibodies specific to *B. burgdorferi* present in a positive sample are already complexed with the gold-labeled antigen-conjugate. The labeled antigen-antibody complex moves to the test line where immobilized antigen captures labeled antigen-antibody complexes via the second binding site on the antibody. Protein A/G-gold conjugate present in the conjugate mixture binds to the Fc region of the target antibody and amplifies the test signal. Free labeled antigen and the rest of the reaction mixture passes through to the control line where the Protein A gold conjugate is captured by the control capture which comprises a chicken anti-Protein A antibody. In this instance, the device is read at about 8 minutes. The appearance of a red line in the test zone and a second red line in the control zone indicates the presence of antibodies to *B. burgdorferi*. The appearance of a line in the control zone only indicates the absence of antibodies to *B. burgdorferi*. The test is considered invalid if (a) the test line appears but no control line forms or (b) neither control nor test line form.

Example 1: Protein A Enhances Specific Detection of Antibody in a Lyme Disease-Specific Lateral Flow Assay Tests were performed to determine the impact of adding Protein A-CGC (colloidal gold conjugate) to a Lyme disease-specific lateral flow assay, while testing a negative sample, a Lyme-positive sample, and a low-level Lyme-positive sample. The purpose was to observe and classify the effect of Protein A-CGC on potential false signal(s) while maintaining adequate sensitivity of the assay. Various Protein A-CGC concentrations were tested in relation to a Protein A-CGC negative control. The lateral flow assay performed in this test is similar to that illustrated in FIGS. 2 and 3. The results are shown in Table 1 below, as indicated by the Reactivity score (scale of 0-5 where a higher number indicates a positive result).

TABLE 1

Summary of Test Results (Reactivity Score)

| | Testing Condition: | | | | | |
|---|---|---|---|---|---|---|
| | Low Pos WB 1:8 Dilution CB25 Pre-Mix | Low Pos WB 1:8 Dilution CB25 Pre-Mix | Dolly Pos WB 1:8 Dilution CB25 Pre-Mix | Dolly Pos WB 1:8 Dilution CB25 Pre-Mix | Neg_345 Plasma 1:8 Dilution CB25 Pre-Mix | Neg_345 Plasma 1:8 Dilution CB25 Pre-Mix |
| Control: NO Protein A | 0 | 0.25 | 1.5 | 1.5 | 0.25 | 0.25 |
| 1X Protein A | 3.5 | 3.5 | 3.5 | 3.5 | 0.5 | 0.5 |
| 1:2 Dilution Protein A | 3.5 | 3.5 | 3.75 | 3.75 | 0.25 | 0.25 |
| 1:4 Dilution Protein A | 1.25 | 1.25 | 2.25 | 2.25 | 0.25 | 0.25 |
| 1:8 Dilution Protein A | 0.5 | 0.75 | 2 | 2 | 0.25 | 0.25 |

As shown in Table 1, the addition of Protein A-CGC amplified the signal of all Lyme-positive samples tested, and especially enabled detection of the 'low' positive samples. Without Protein A-CGC, the low positive samples were undetectable, showing a Reactivity score comparable to the negative samples (~0.25 or less). In contrast, the addition of Protein A-CGC at 1× concentration and 1:2 dilution amplified the signal significantly, showing a Reactivity score of about 3.5. Protein A-CGC thus significantly improve detection of target antibodies in this Lyme-disease specific lateral flow assay.

Example 2: Protein A Enhances Specific Detection of Antibody in a Lateral Flow Assay Performed on a Stressed Biological Sample Tests were performed to determine the impact of adding Protein A-CGC (colloidal gold conjugate) to a previously stressed 48 BSA (bovine serum albumin)/DAG IgG conjugate mixture. The conjugate mixture was pre-stressed for 15 days in an incubator at 35° C. This experiment tested both stressed and non-stressed samples in the presence or absence of Protein A-CGC. The lateral flow assay performed in this test is similar to that illustrated in FIGS. 2 and 3. The results are shown in Table 1 below, as indicated by the Reactivity score (scale of 0-5 where a higher number indicates a positive result). The results are shown in Table 2 below.

TABLE 2

Summary of Test Results for Stressed v. Non-Stressed Samples

| | Sample | | | |
|---|---|---|---|---|
| | Pos_11-0483 | Pos_11-0483 | Neg_SCA30-2235HI | Neg_SCA30-2235HI |
| | Temperature | | | |
| | 2-8° C. | 35° C. | 2-8° C. | 35° C. |
| Day 1 | 2.25 | 2.0 | 0 | 0 |
| Day 15 | 2.5 | 0.75 | 0 | 0 |
| Day 15 + PA | 2.75 | 1.25 | 0 | 0 |

As shown in Table 2 above, the addition of Protein A-CGC to the lateral flow assay mixture amplified the signal of the day 15 stressed (35° C.) biological sample relative to the absence of Protein A-CGC, as shown by an increased Reactivity score from 0.75 to 1.75. The day 15 non-stressed sample (2-8° C.) was also slightly affected by addition of Protein A-CGC, as shown by the increased Reactivity score from 2.25 to 2.75. Also, the negative samples were not altered by addition of Protein A-CGC.

To the extent that any definitions in documents incorporated by reference are inconsistent with the definitions provided herein, the definitions provided herein are controlling. Although the invention has been described with reference to the presently preferred embodiments, it should be understood that various changes and modifications, as would be obvious to one skilled in the art, can be made without departing from the spirit of the invention. Accordingly, the invention is limited only by the following claims.

What is claimed:

1. A capture complex comprising a capture entity immobilized on a surface, an antibody, a first detector, and a second detector, wherein the capture entity binds to a variable region of the antibody and wherein the first detector comprises a Fc-binding molecule conjugated to a first detectable entity, wherein the Fc-binding molecule of the first detector is bound to the Fc region of the antibody, and wherein the second detector comprises an antigen or antigenic peptide specifically bound to a variable region of the antibody.

2. The capture complex of claim 1, wherein the capture complex is immobilized on a test region of the surface.

3. The capture complex of claim 1, wherein the second detector is conjugated to a second detectable entity.

4. The capture complex of claim 3, wherein the first and second detectable entities are gold nanoparticles.

5. The capture complex of claim 3, wherein the first detector and the second detector are present in a ratio of about 20:1 to about 1:1.

6. The capture complex of claim 1, wherein the Fc-binding molecule is protein A and/or protein G.

7. The capture complex of claim 6, wherein the Fc-binding molecule comprises protein A and protein G, and wherein protein A and protein G are present in a ratio of about 10:1 to about 1:10.

8. The capture complex of claim 1, wherein the capture entity is an antigen or antigenic peptide.

9. The capture complex of claim 1, wherein the wherein the capture entity is an antigen or antigenic peptide from an organism selected from the group consisting of heartworm, *Ehrlichia canis, Ehrlichia chaffeensis, Ehrlichia ewingii, Borrelia burgdorferi, Borrelia afzelii, Borrelia garinii, Anaplasma phagocytophilum, Anaplasma platys*, feline leukemia virus, parvovirus, influenza A strain, influenza B strain, avian influenza virus, respiratory syncytial virus, *Legionella*, adenovirus, rotavirus, feline immunodeficiency virus, human immunodeficiency virus, and Group A *Streptococcus*.

10. The capture complex of claim 1, wherein the first detectable entity is a metal nanoparticle, metal nanoshell, fluorophore, or colored latex particle.

11. The capture complex of claim 10, wherein the metallic nanoparticle or metallic nanoshell is selected from the group consisting of gold particles, silver particles, copper particles, platinum particles, cadmium particles, composite particles, gold hollow spheres, gold-coated silica nanoshells, and silica-coated gold shells.

12. The capture complex of claim 1, wherein the surface is a flow path in a lateral flow assay device, a surface of a microtiter plate or a flow path in an analytical rotor.

* * * * *